United States Patent
Loureiro et al.

(10) Patent No.: US 10,512,410 B2
(45) Date of Patent: Dec. 24, 2019

(54) SYSTEM AND METHOD FOR OPERANT LEARNING BRAIN MACHINE INTERFACE BY RECEIVING ELECTRODES AND NEURAL SIGNALS AT NEURAL PROCESSOR

(71) Applicant: FUNDAÇÃO D. ANNA SOMMER CHAMPALIMAUD E DR. CARLOS MONTEZ CHAMPALIMAUD, Lisbon (PT)

(72) Inventors: Nuno Loureiro, Lisbon (PT); Vitor B. Paixão, Lisbon (PT); Rui M.Costa, Lisbon (PT); Fernando Santos, Lisbon (PT)

(73) Assignee: FUNDAÇÃO D. ANNA SOMMER CHAMPALIMAUD E DR. CARLOS MONTEZ CHAMPALIMAUD, Lisbon (PT)

( * ) Notice: Subject to any disclaimer, the term of this patent is extended or adjusted under 35 U.S.C. 154(b) by 0 days.

(21) Appl. No.: 15/744,865

(22) PCT Filed: Jul. 13, 2016

(86) PCT No.: PCT/IB2016/054179
§ 371 (c)(1),
(2) Date: Jan. 15, 2018

(87) PCT Pub. No.: WO2017/009787
PCT Pub. Date: Jan. 19, 2017

(65) Prior Publication Data
US 2018/0199840 A1     Jul. 19, 2018

(30) Foreign Application Priority Data

Jul. 13, 2015  (PT) .......................... 108690

(51) Int. Cl.
*A61B 5/04* (2006.01)
*A61B 5/00* (2006.01)
(Continued)

(52) U.S. Cl.
CPC .......... *A61B 5/04001* (2013.01); *A61B 5/048* (2013.01); *A61B 5/0482* (2013.01);
(Continued)

(58) Field of Classification Search
CPC ........................... A61B 5/048; A61B 5/04001
See application file for complete search history.

(56) References Cited

U.S. PATENT DOCUMENTS

| | | | |
|---|---|---|---|
| 10,080,506 B2 * | 9/2018 | Fu | A61B 5/0476 |
| 2006/0167371 A1 * | 7/2006 | Flaherty | A61F 2/50 600/545 |

(Continued)

*Primary Examiner* — Tammara R Peyton
(74) *Attorney, Agent, or Firm* — Mark M. Friedman

(57) ABSTRACT

A method, system and computer readable media for a BMI using a fixed decoder based on ratios of different frequency bands, making the decoder robust, less jittery, and resistant to artifacts. The fixed decoder can be configured to use a limited subset of available channels. The decoder can therefore be optimized for each human subject (frequency bands to use, ratios to process the received signals, which channels, weights, etc.) and then fixed. Output from the fixed decoder can be provided to a training program that implements specific feedback and training parameters, thereby enabling subjects to learn to control devices rapidly, as well as consolidate this control. The training program provides continuous feedback of the current transformation being output by the fixed decoder in conjunction with feedback of the past transformations (e.g., up to a second before) and saliency of the feedback when goals of the task are achieved.

20 Claims, 11 Drawing Sheets

(51) Int. Cl.
*A61B 5/048* (2006.01)
*A61B 5/0482* (2006.01)
*G06F 3/01* (2006.01)
*A61F 2/72* (2006.01)
*A61F 4/00* (2006.01)
*A61B 5/0478* (2006.01)

(52) U.S. Cl.
CPC .............. *A61B 5/7267* (2013.01); *A61F 2/72* (2013.01); *A61F 4/00* (2013.01); *G06F 3/015* (2013.01); *A61B 5/0478* (2013.01); *A61B 5/6814* (2013.01)

(56) References Cited

U.S. PATENT DOCUMENTS

| | | | |
|---|---|---|---|
| 2012/0071780 A1* | 3/2012 | Barachant | A61B 5/04012 600/544 |
| 2015/0012111 A1* | 1/2015 | Contreras-Vidal | A61B 5/4851 623/25 |
| 2016/0129251 A1* | 5/2016 | Watt | A61N 1/37282 607/45 |
| 2018/0021579 A1* | 1/2018 | Kahana | A61N 1/0531 607/45 |

\* cited by examiner

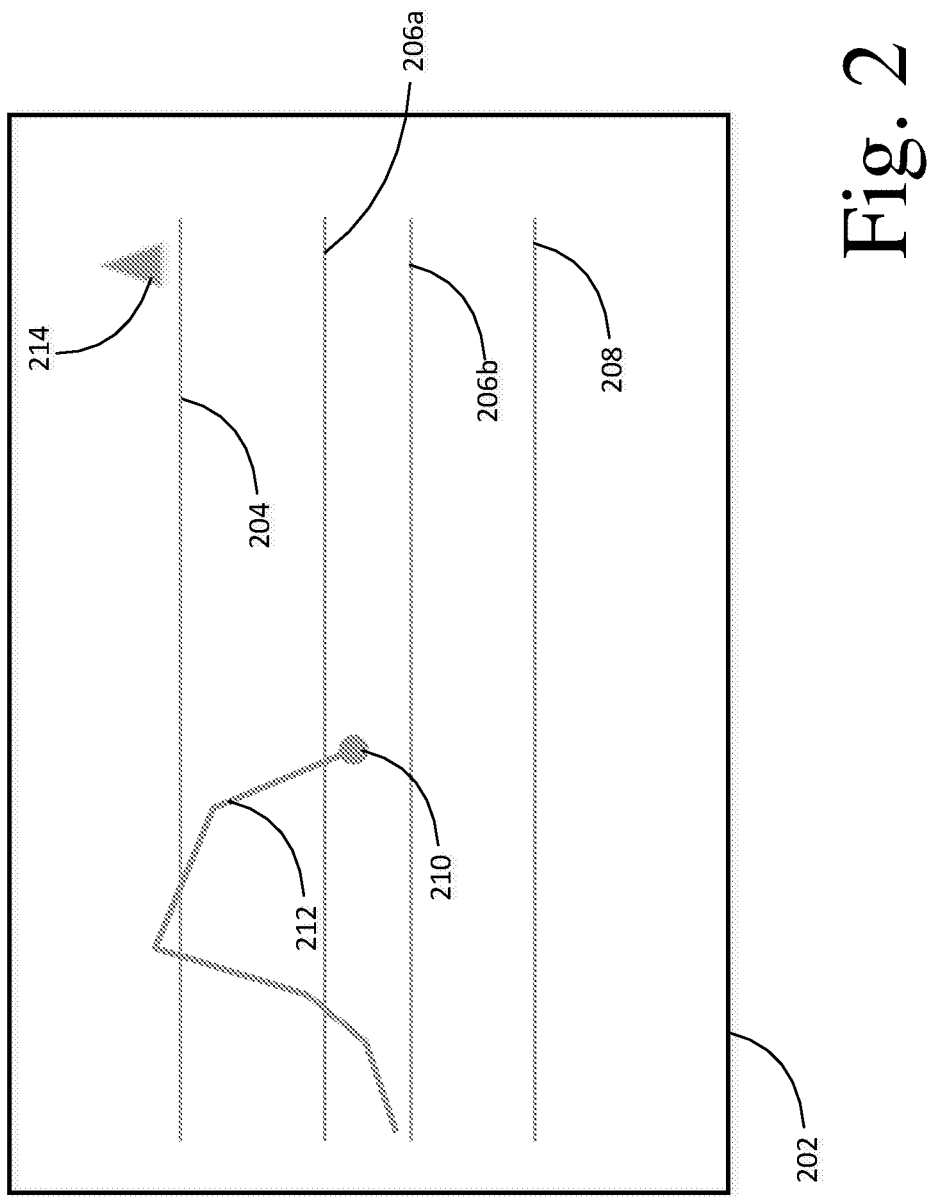

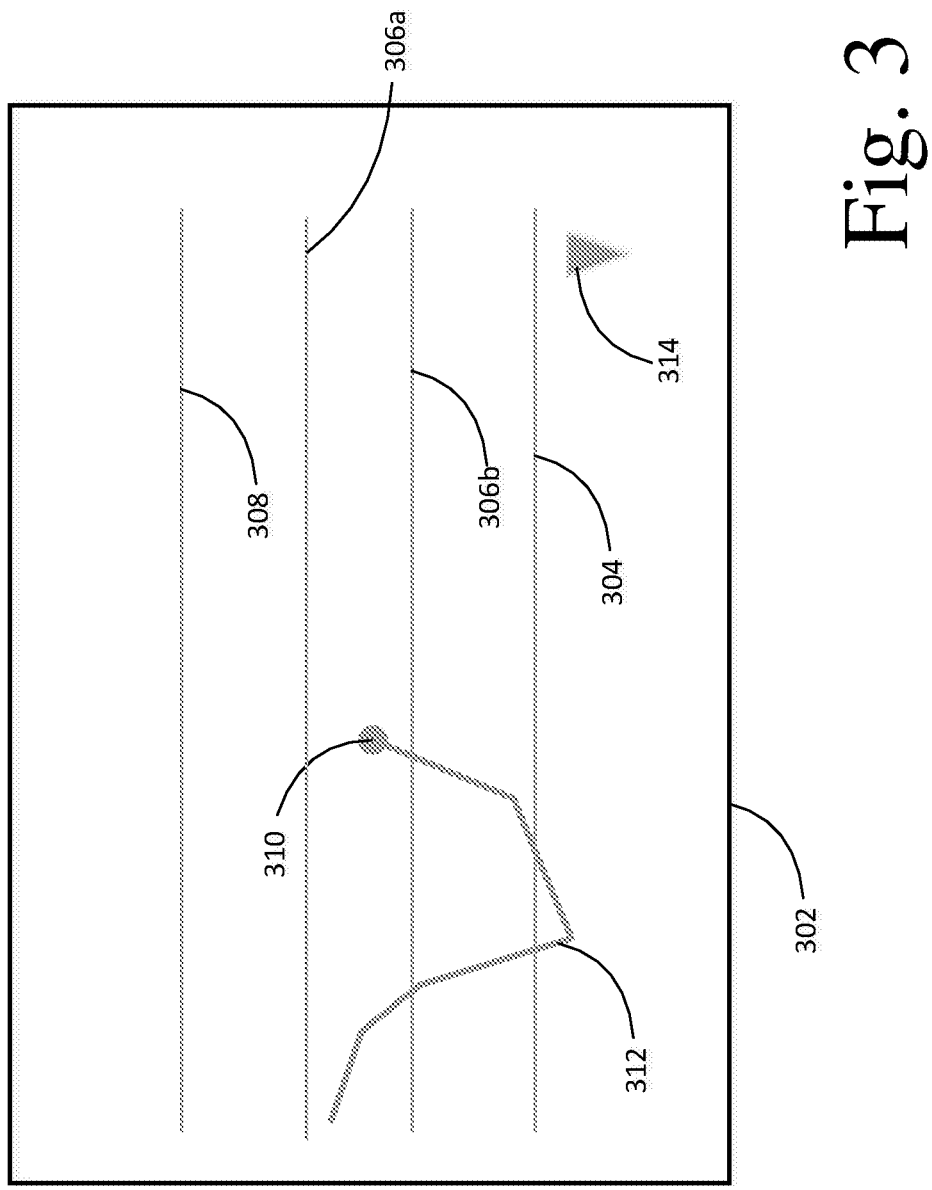

SYSTEM AND METHOD FOR OPERANT LEARNING BRAIN MACHINE INTERFACE BY RECEIVING ELECTRODES AND NEURAL SIGNALS AT NEURAL PROCESSOR

BACKGROUND OF THE INVENTION

The invention described herein generally relates to an operant learning brain-machine interface. In particular, the invention relates to systems, methods and computer program products for implementing an EEG-based brain machine interface utilizing a fixed decoder, the output of which can drive or otherwise operate a variety of machines and prosthetics.

DESCRIPTION OF THE RELATED ART

A Brain Machine Interface (BMI) is a direct communication pathway from a brain to an external device. This communication can be achieved by using a recording device that measures neural activity, with the recording device transmitting the measured neural activity to a computer (or any other programmable device, including hardware and software) that transforms and interprets the signal. The computer feeds the signal into an actuator or external device, with the external device providing feedback to the user as to performance, thereby closing the loop.

Basic research regarding BMIs has moved at a stunning pace since the first demonstrations in the late 1990's in which experiments conclusively demonstrated that ensembles of cortical neurons could directly control a robotic manipulator. Indeed, the primary purpose or use of BMIs to date has been as a potential new therapy to restore motor control in severely disabled patients, such as those suffering from diseases or other medical conditions that effect the movement of a patient, particularly conditions involving the central nervous system. For example, as suggested above, exoskeletons or other manner of assistive mechanical technologies can benefit from integration with a BMI to provide newfound freedom to individuals previously confined due to limited mobility. Similarly, artificial or bionic limbs harnessing such interfaces provide the ability for direct control of a prosthesis by a user through the use of neural signals, as opposed to limited mechanical manipulation, thereby bringing freedom of actuation and manipulation approaching that offered by a natural limb.

A feature that distinguishes BMIs is whether they utilize invasive techniques, such as intra-cranial implants, or implement non-invasive methods to obtain neural signals. Whether using either invasive or non-invasive techniques to obtain neural signals, however, information contained in the signals must be interpreted such that meaningful action can be taken based on such information. One approach for the design of a BMI system is known as the decoding approach. Using this technique, a mathematical model is generated by a computer to relate (decode) the recorded neural activity to natural limb movements, thereby learning the "meaning" of received neural signals as a function of time. This activity can then be used to predict movements from neural activity alone. Most commercial systems in the market are approaching BMI through different variants of this paradigm.

An exemplary system that implements the decoding technique is discussed in WO 2014/025772, entitled "Systems and Methods for Responsive Neurorehabilitation", by Babak, et al. In Babak, the author proposes receiving neural signals through the use of an adaptive feature decoder, which functions to extract specific signals from a plurality of neural signals that the system typical receives from a user's brain. Babak then provides the extracted signal(s) to an adaptive motor decoder, which is configured to map the extracted signal(s) to a command signal of a rehabilitation device. The command signal is output, thereby controlling the device, as well as causing the generation and receipt of sensory feedback from the user. This sensory feedback is also extracted by the adaptive feature decoder and passed to the adaptive motor decoder, which adjusts its internal mapping parameters accordingly. In this manner, the rehabilitation device of Babak dynamically adapts output control based on the decoded signals that it receives from the user.

The decoding approach requires sensory and other stimuli information, which have already been encoded within the brain of an operant, to be reconstructed within the context of a digital computer. Such reconstruction within a digital computer typically utilize neural networks or similar constructs to predict received stimuli based on incoming neural signals and require a complex approximation or model of the operant. In other words, software attempting to implement such an approach is required to adapt itself to incoming neural signals by matching or otherwise mapping such neural signals to a desired outcome that is congruent with the input that it is receiving. Such an approach suffers from numerous drawbacks such as implicit limitations of machine learning technologies, difficulty in troubleshooting problems where training outcomes are nondeterministic and depend on initial parameters, an inability to add later acquired data to retrain an existing model, etc. Other decoding techniques attempt to solve these and other drawbacks, but are accompanied by other drawbacks and limitations as well.

Novel systems and methods are therefore needed to harness the dynamics of neural changes that allow for the generation of command signals, which custom business logic can then utilize to perform specific, arbitrary tasks.

SUMMARY OF THE INVENTION

The present invention provides systems, methods and computer program products that utilize a fixed decoder in conjunction with the collection of brain signal activity using non-invasive electrodes to generate output signals that can be used to perform fixed tasks. The present invention rapidly allows a user to learn to control a device through control of a fixed decoder, which improves over time with continued use of the invention.

Embodiments of the present invention provide various novel improvements to a BMI, including the use of a fixed decoder based not in the power of single EEG frequency bands, but rather on ratios of different frequency bands, making the decoder robust, less jittery, and resistant to artifacts. Program logic for the fixed decoder can be instantiated in software as well as hardware (e.g., a Field-Programmable Gate Array), and can be configured to use a limited subset of channels that are available to the fixed decoder. Accordingly, the decoder can be optimized for each human subject or task (which frequency bands to use, which particular ratios or algorithms to process the received signals, which channels, which weights, etc.) and then fixed, in either hardware or software, so that a given subject can learn to control a variety of devices using the decoder (provided that the control commands use the same transformation or transformations).

Output from the fixed decoder can be provided to a training program that implements specific feedback and training parameters, thereby enabling subjects to learn to control devices rapidly, as well as consolidate this control. The training program provides continuous feedback of the current transformation being output by the fixed decoder in conjunction with feedback of the past transformations (e.g., up to a second before) and saliency of the feedback when goals of the task are achieved.

In view of the foregoing, embodiments of the invention are directed towards a method for generating an output command by a neural processor through use of an operant learning brain-machine interface. The invention in accordance with this embodiment comprises selecting one or more electrodes from a plurality of electrodes by program code executing on the neural processor and receiving neural signals at the neural processor from the one or more selected electrodes. Thresholds are set based on the received neural signals, as well as a timer at the neural processor to define an output command rate. While the timer has not elapsed, the neural processor executes program code for retrieving and processing the received neural signals and calculates a control command through use of a fixed decoder in the neural processor that receives the retrieved and processed neural signals as input.

In situations where the neural processor is connected to a user, receiving neural signals by the neural processor comprises receiving neural signals from the operant, e.g., via the electrodes that can be affixed to the cranium of the operant. When in operation, the neural processor can execute a check by executing program code to determine if a current task is complete. As part of task completion, program code executing on the neural processor can set a timer to define a subsequent output command rate, as well as retrieve and processes the received neural signals while the timer has not elapsed. Program code executing on the neural processor can provide such control commands as an input to a subsequent hardware or software component.

The set of electrode selection is broken into a sub-process in accordance with one embodiment of the present invention. More specifically, selecting one or more electrodes from a plurality of electrodes can comprise presenting a task to the operant, the task under the control of program code executing at the neural processor, and acquiring neural activity of the operant during presentation of the task by the neural processor. The neural processor applies selection criteria to the acquired neural activity and selects one or more electrodes that exceed the selection criteria. Similarly, selecting electrodes by the neural processor comprises selecting a subset of electrodes by the neural processor that exceed the selection criteria. Acquiring neural activity can further comprise starting an electrode selection timer by program code executing at the neural processor to define a window over which the neural processor is to acquire neural activity.

The neural processor can be operative to process the neural signal that it receives. According to embodiments of the present invention, processing the received neural signals comprises attenuating signal noise on one or more channels contained within the received neural signals and calculating a spectral density for the one or more attenuated channels. Mean power is determined in one or more selected bands for the one or more channels and power ratios are determined for the one or more channels. Determining power ratios for a given channel from the one or more channels is determined according to one embodiment by program code executing on the neural processor to calculate the ratio $$\frac{\gamma \cdot \theta}{\beta \delta}.$$

calculating the control command according to various embodiment comprises program code instructing the neural processor to calculate $$\log \sum_{chn=1}^{n} ratio_{chn(n)}$$

In addition to the foregoing, the scope of the present invention captures non-transitory computer readable media comprising program code that when executed by a programmable processor causes execution of a method for generating an output command by a neural processor through use of an operant learning brain-machine interface. The program code according to one embodiment comprises program code for selecting one or more electrodes from a plurality of electrodes by program code executing on the neural processor and program code for receiving neural signals at the neural processor from the one or more selected electrodes. Program code is provided for setting thresholds based on the received neural signals and setting a timer at the neural processor to define an output command rate. The present embodiment further provides program code for processing the received neural signals by the neural processor while the timer has not elapsed and for calculating a control command through the use of a fixed decoder in the neural processor that receives the retrieved and processed neural signals as input.

Additionally, program code can be supplied as part of the neural processor for providing the control command as an input to a subsequent hardware of software component. Such program code may also comprise program code for performing a check on the neural processor to determine if a current task is complete, as well as program code for setting the timer to define a subsequent output command rate and program code for retrieving and processing the received neural signals while the timer has not elapsed.

The neural processor can select electrodes from which it collects neural signals for processing. As such, program code for selecting one or more electrodes from a plurality of electrodes can comprise program code for presenting a task to the operant and program code for acquiring neural activity of the operant during presentation of the task by the neural processor. Further portions of program code can apply selection criterial by the neural processor to the acquired neural activity and select, by the neural processor, one or more electrodes that exceed the selection criteria. The program code for selecting one or more electrodes can also comprise program code for selecting a subset of electrodes by the neural processor that exceed the selection criteria.

In processing neural signals, the program code for processing the received neural signals cam comprise program code for attenuating signal noise on one or more channels contained within the received neural signals and calculating a spectral density for the one or more attenuated channels. Program code executing at the neural processor further comprises program code for determining mean power in one or more selected bands for the one or more channels and program code for determining power ratios for the one or more channels. Program code for calculating the control command according to one embodiment comprises program $$\log \sum_{chn=1}^{n} ratio_{chn(n)}$$

BRIEF DESCRIPTION OF THE DRAWINGS

The invention is illustrated in the figures of the accompanying drawings which are meant to be exemplary and not limiting, in which like references are intended to refer to like or corresponding parts, and in which:

FIG. 2 illustrates a user interface for a training application according to one embodiment of the present invention;

FIG. 3 illustrates a user interface for a training application according to another embodiment of the present invention;

DETAILED DESCRIPTION OF THE INVENTION

Subject matter will now be described more fully hereinafter with reference to the accompanying drawings, which form a part hereof, and which show, by way of illustration, exemplary embodiments in which the invention may be practiced. Subject matter may, however, be embodied in a variety of different forms and, therefore, covered or claimed subject matter is intended to be construed as not being limited to any example embodiments set forth herein; example embodiments are provided merely to be illustrative. It is to be understood that other embodiments may be utilized and structural changes may be made without departing from the scope of the present invention. Likewise, a reasonably broad scope for claimed or covered subject matter is intended. Among other things, for example, subject matter may be embodied as methods, devices, components, or systems. Accordingly, embodiments may, for example, take the form of hardware, software, firmware or any combination thereof (other than software per se). The following detailed description is, therefore, not intended to be taken in a limiting sense.

Throughout the specification and claims, terms may have nuanced meanings suggested or implied in context beyond an explicitly stated meaning. Likewise, the phrase "in one embodiment" as used herein does not necessarily refer to the same embodiment and the phrase "in another embodiment" as used herein does not necessarily refer to a different embodiment. It is intended, for example, that claimed subject matter include combinations of example embodiments in whole or in part.

Figure 1A:
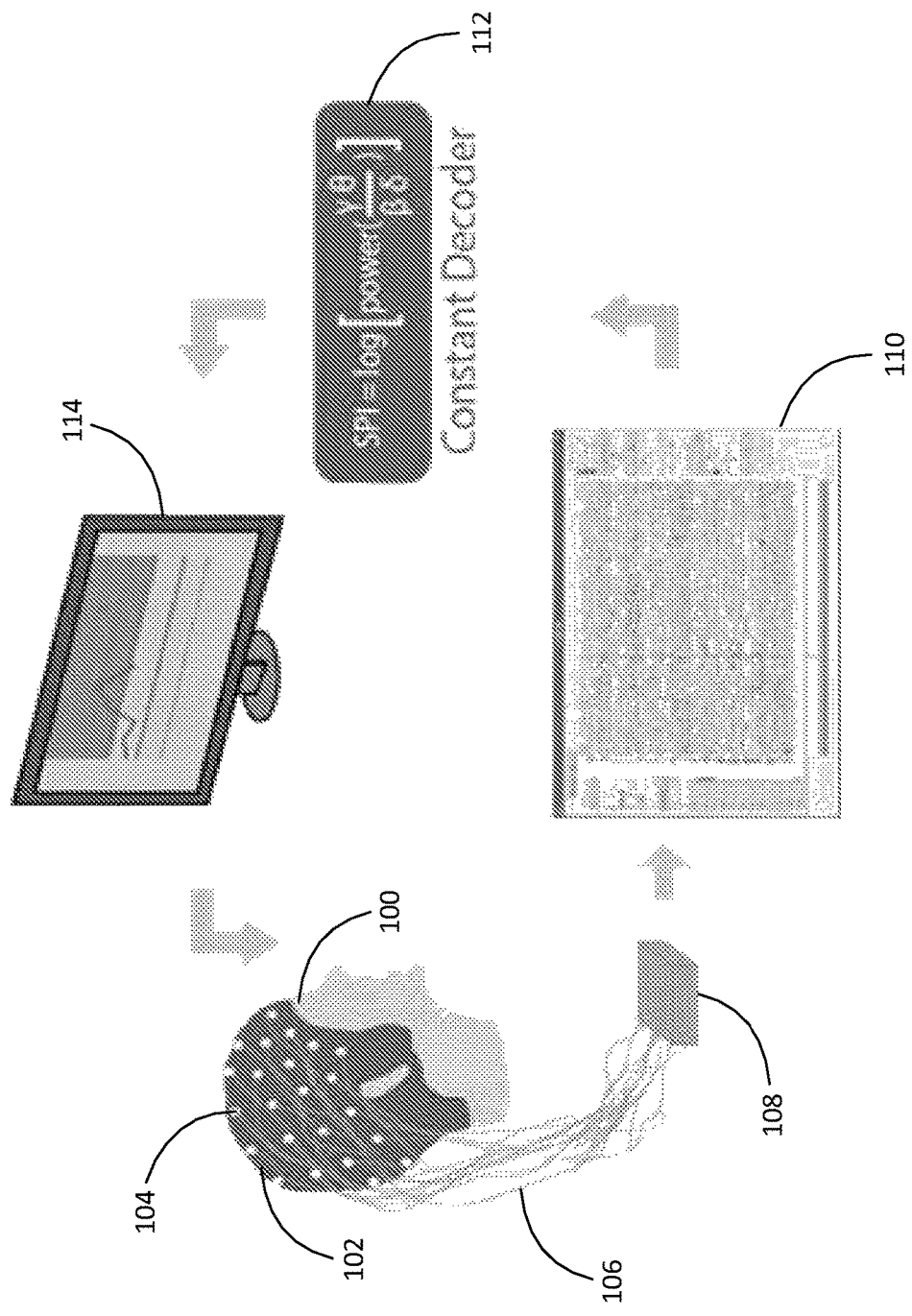
FIG. 1A presents a system diagram illustrating an overall brain machine interface utilizing a fixed decoder according to one embodiment of the present invention.

FIG. 1 illustrates an overall brain machine interface utilizing a fixed decoder according to one embodiment of the present invention; specifically, the closed loop relationship between these various components. The system of FIG. 1 comprises a plurality of electrodes 104 that are affixed to the scalp of a user 100, which can be affixed or otherwise maintained in place by way of a cap or similar garment 102 that maintains the spatial placement of the electrodes 104 on the scalp. Each of the plurality of electrodes are in communication with a neural processor 108 via individual leads 106, which are typically formed of metallic wires that serve as a conduit for the signals received by a given electrode 104.

The neural processor 108 comprises hardware and software operative to obtain neural signals collected by one or more of the plurality of electrodes 104 in contact with the scalp of the user 100. According to various embodiments, the neural processor 108 can collect the received neural signals for local storage and processing in near real time or can process the signals in real-time as the signals are received by the neural processor 108. In either embodiment, the neural processor 108 receives a set of neural signals, which can be graphically represented 110 in accordance with the various frequency bands collected by the electrodes 104, e.g., delta, theta, alpha and beta waves.

The neural processor 108 can utilize neural signals that it receives from each of the electrodes 104 attached to the scalp of the user 100. Alternatively, the neural processor 108 can select a subset of the available electrodes through which it is receiving neural signals, limiting process to neural signals received from the selected electrodes 104. The neural processor 108 extracts the various frequency bands contained in the neural signals received from the electrodes 104 under consideration, e.g., using spectral techniques well known to those of skill in the art, and passes values for the various bands at a given moment in time to a fixed decoder 112. Based on the values of the various bands at a given moment in time, the fixed decoder 112 calculates an output value that can be utilized as a control command by an application 114 to perform a specific, arbitrary task.

The neural processor 108 continually receives neural signals from the electrodes 104 and extracts various bands, which are passed to a fixed decoder 112 that generates output values that are used by an application 114 to perform a task. In this manner, the user 100 can continue to send signals over a period of time to interact with the application. For example, the fixed decoder 112 can output a command signal representing the position of a cursor over a period of time, a direction to move an object on a display, etc. As the user 100 interacts with the neural processor 108, he or she receives feedback from the user interface of the application 114, e.g., the cursor moves in a particular direction. By providing feedback from the user interface, the user 100 can rapidly learn to control specific, arbitrary tasks that an application presents, as well as consolidate such control.

Figure 1B:
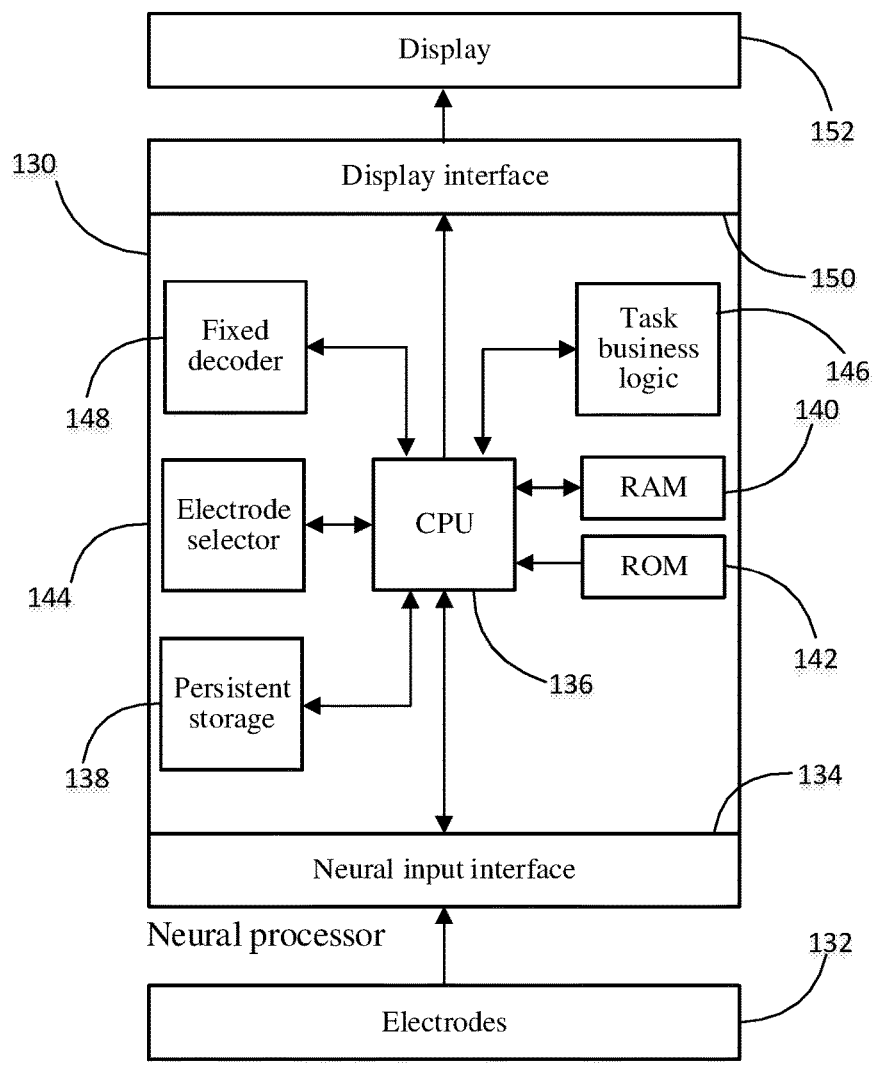
FIG. 1B presents a block diagram illustrating a neural processor that utilizes a fixed decoder to perform a task according to one embodiment of the present invention.

FIG. 1B presents a block diagram illustrating a neural processor that utilizes a fixed decoder to perform a task according to one embodiment of the present invention. The neural processor 130 of FIG. 1B is in communication with both a set of one or more electrodes 132 and a display device 152. In operation, the neural processor 130 receives neural signals from the set of one or more electrodes 132 and processes the received neural signals using a fixed decoder 148. The fixed decoder 148 outputs command signals for use by an application 136, as well as feedback to a display device 152 regarding the command signal that was calculated based on the neural signals generated by the user. It should be noted that the display 152 could be replaced with any number of end peripherals to be controlled by embodiments of the present invention. For example, instead of a display, the command signal output by the fixed decoder 148 can be interpreted by business logic for a flight control application, such that display 152 and its associated display interface 150 are substituted with a flight control interface and flight controls. Similarly, command signals can be used to control a wheelchair, prosthetic limb or virtually any other devices that requires the receipt of command signals, such as directional command signals.

Focusing on the embodiment that FIG. 1B illustrates, a number of electrodes 132 are in communication with the neural processor 130 over a neural input interface 134. The neural input interface 134, under the control of the central processing unit 136, which is itself executing instructions received from RAM 140 or ROM 142, executes one or more routines to clean up or otherwise amplify specific bands contained within the neural signals that the neural processor is receiving from the electrodes. Techniques for the selection of specific electrodes and frequency bands comprising the same are described in greater detail herein.

In addition to the neural input interface 134 and display interface 150, the neural processor 130 comprises a central processing unit ("CPU") 136, RAM 140 and ROM 142, persistent storage 138, an electrode selector module 144, a fixed decoder 148 and task-specific business logic 146. The CPU 136 is the main control component of the neural processor 130, and can execute instructions on behalf of, or in conjunction with, other components comprising the neural processor 130. Although presented as disparate components or modules, program logic comprising the electrode selector 144, fixed decoder 148 and task business logic 146 can be implemented according to various embodiments as software applications or routines that are stored in random 140 or persistent storage 138 for execution by the CPU.

As illustrated, the neural processor 130 has access to several data storage structures that provide transient 140, persistent 138 and permanent 142 storage for data and program code. Persistent storage 138 provides storage of data and program code between sessions when the neural processor 130 enters a power down state. Exemplary persistent 138 storage includes, but is not limited to, hard disk drives, flash memory, each of which allows the neural processor to maintain program code as well as collected neural signals from one or more users over a given period of time. Transient storage, such as RAM 140, provides a high-speed memory space for the CPU to maintain executing program code and any data necessary to execute such program code, whereas permanent memory, such as ROM 142, provides read-only instructions typically used by the CPU at startup and initialization.

As indicated, the neural processor 130 also comprises an electrode selector 144, a fixed decoder 148 and task business logic 146. The electrode selector 130 is operative to execute one or more routines (that it can execute in conjunction with processing by the CPU), which select the specific electrodes from which neural signals are read and extract frequency bands for processing. The frequency bands that the electrode selector 144 outputs are provided as input to the fixed decoder 148, which outputs a control value or signal that it can calculate on the basis of the power levels for the specific frequency bands that electrode selector 144 provides as input to the fixed decoder 148.

The fixed decoder 148 outputs the command signal to task business logic 146 that is operative to perform a task based on the instruction embodied in the command signal. According to one embodiment, a command signal below a certain value serves as a command to the task business logic to redraw a display screen in a certain manner, manipulate a cursor in a certain dimension, etc. Task business logic 146 is task specific and can be modified depending on the specific task to which the business logic is directed. The task business logic 146 can programmed in various combinations of hardware and software to respond to command signal from the fixed decoder 148 in a particular manner. For example, where the task is to control a cursor on a screen, the task business logic can be programmed to take certain action as to the display of the cursor based on the command signals that it receives from the fixed decoder.

FIGS. 2 and 3 illustrate user interfaces for a training application according to various embodiments of the present invention. The user interfaces of FIGS. 2 and 3 represent embodiments of output from task business logic in which the task business logic is operative to instruct a processor to display a user interface and manipulate a cursor displaced within user interface based on command signals that the business logic receives from a fixed decoder. Starting with FIG. 2, the user interface is presented to the user within a display device 202 as various graphics. The user interface on the display 202 presents a task for the user to complete, which in the present embodiment is requesting that the user attempt to manipulate a cursor 210 across an upper target line 204. The requirements of the task are communicated to the user by way of a visual command or cue, represented by an upward pointing arrow 214 disposed of in the upper right hand corner of the interface on the display 202.

In addition to the immediate task presented to the user, the user interface on the display 202 provides the user with historical feedback 212 as to the position of the cursor 210 on the display 202 as a function of time. In this manner, the user can make historical observations as to the output of the fixed decoder and modify the power of various frequency bands that contained in the neural signals that the neural processor is receiving. This visual trail of historical feedback 212 that the processor is programmed to display can be increased or decreased, but in either event represents the historical position of the cursor in 2D space during the current session for a current user.

As the user interacts with the neural processor by sending neural signals to the neural processor, the fixed decoder calculates or otherwise generates command signals, which task business logic uses to position the cursor on the display 202. When the user satisfies a current task, which in the present embodiment is to position the cursor above an upper target line 204 presented on the display 202 as indicated by cue 214, the program code controlling the display 202 can instruct the processor to present or otherwise project an indication of task satisfaction, e.g., displaying a visual indication or text indicative of success. Although the exemplary task business logic receives command signals from the fixed decoder to render the cursor on the display 202 in 2D space, task business logic can also control rendering and display of other user interface components on the display 202. Alternatively, or in conjunction with task business logic, other program code that the CPU executes can control rendering and display of other user interface components on the display 202.

In addition to the foregoing user interface components, the display also renders two inner reset lines 206a and 206b, as well as a lower target line 208. The lower target line 208, like the upper target line, serves as a visual threshold across which the user must manipulate the cursor to satisfy certain tasks, as is discussed in greater detail herein. The reset lines 206a and 206b allow the user to reset the current task by keeping the cursor in between the two inner reset lines for a certain period of time.

Similar to FIG. 2, FIG. 3 illustrates a user interface that is presented to the user within a display device 302 as various graphics. The user interface on the display 302 presents a task for the user to complete, which in the present embodiment is requesting that the user attempt to manipulate a cursor 310 across a lower target line 304. A visual command or cue communicates the requirements of the task to the user, which in the present embodiment is represented by a downward pointing arrow 314 disposed of in the lower right hand corner of the interface on the display 302.

In addition to the immediate task presented to the user, the user interface on the display 302 provides the user with historical feedback 312 as to the position of the cursor 310 on the display 302 as a function of time. In this manner, the user can make historical observations as to the output of the fixed decoder and modify the power of various frequency bands contained in the neural signals that the neural processor is receiving. This visual trail of historical feedback 312 can be increased or decreased, but in either event represents the historical position of the cursor in 2D space during the current session for a current user.

When the user satisfies a current task, which in the present embodiment is to position the cursor above a lower target line 304 presented on the display 302 as indicated by cue 314, the program code controlling the display 302 can present or otherwise project an indication of task satisfaction, e.g., displaying a visual indication or text indicative of success. Although the exemplary task business logic receives command signals from the fixed decoder to render the cursor on the display 302 in 2D space, task business logic can also control rendering and display of other user interface components on the display 302. Alternatively, or in conjunction with task business logic, other program code that the CPU executes can control rendering and display of other user interface components on the display 302. In addition to the foregoing user interface components, the display also renders two reset lines 306a and 306b, as well as an upper target line 308, both of which function in a manner analogous to that described in conjunction with FIG. 2.

As described above, the user interfaces illustrated by FIGS. 2 and 3 can be part of task business logic requiring the user to manipulate a cursor in 2D space over a period of time. According to one embodiment, the task consists of three ten-minute (10) engaged runs per day, throughout a training period of ten (10) days (for example, one session per day, during two weeks with a 2-day break in between). During the testing period, the neural activity of a set of EEG electrodes is recorded and simultaneously transformed using the fixed decoder, which information is used to set the position of a cursor on a display. Both the decoder and selected electrodes are only established once, during the first session, and do not change throughout the training period.

According to one embodiment, the task is designed as follows: the user is shown a cue, e.g., cue 214 or cue 314, indicating one of two possible target areas to where the cursor is to be directed, e.g., above upper control line 204 or below lower control line 208. A pleasing visual indication is presented if the correct target is reached, which can include a colorful patch filling the screen, thereby providing the user with positive reinforcement. This is considered a correct trial. On the other hand, if the incorrect target is reached or the thirty (30) seconds run out, no reinforcement is given and the trial ends as incorrect. In order to restart a new trial, the user needs to keep the cursor in a center position in conjunction with the reset line for two (2) seconds.

Figure 4:
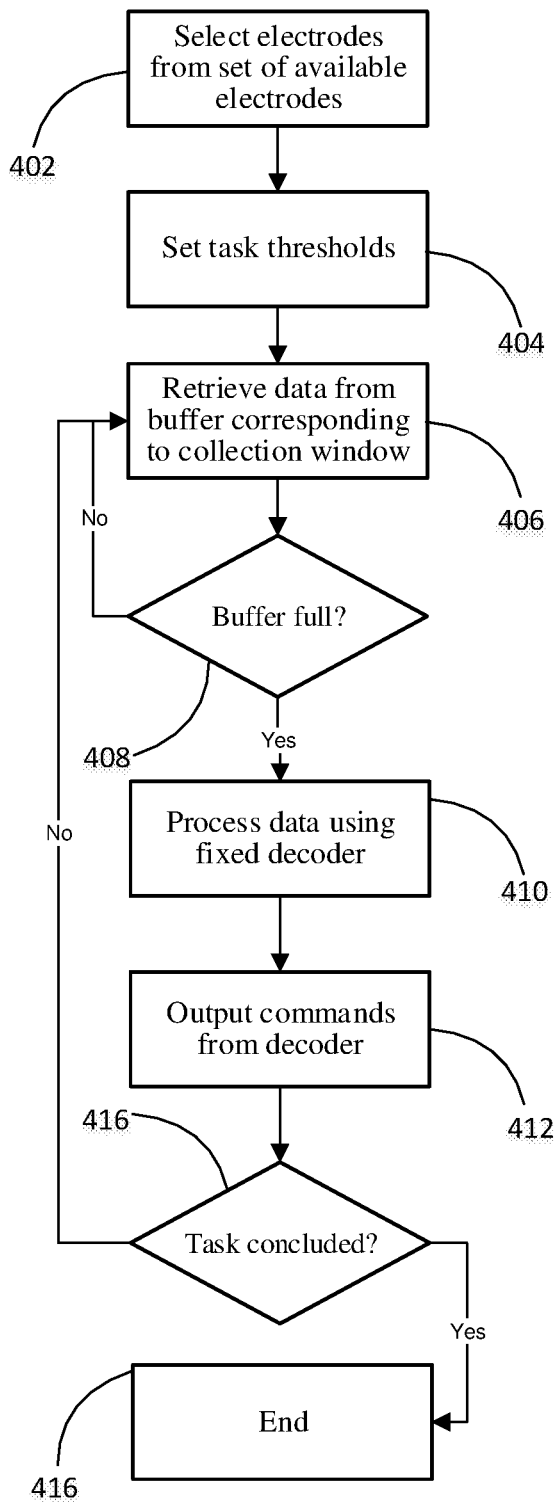
FIG. 4 presents a flow diagram illustrating an overall method for execution of a neural processor utilizing a fixed decoder according to one embodiment of the present invention.

FIG. 4 presents a flow diagram illustrating an overall method for execution of a neural processor utilizing a fixed decoder according to one embodiment of the present invention. As indicated above, the user can be fitted with a plurality of electrodes through which the neural processor captures neural signals for processing. Accordingly, the process of FIG. 4 begins with the selection of electrodes from the set of available electrodes, step 402. Once a determination is made as to the electrodes that are to be used to capture neural signals for the task, thresholds are set for the user based on the neural signals collected, step 404. The processes of electrode selection and setting task thresholds is described in greater detail herein.

According to certain embodiments, EEG acquisition frequency is higher than the processing/feedback frequency (2048 Hz and 4 Hz, respectively). For this reason, the collected EEG data can be stored in a buffer for retrieval at lower frequencies, step 406. A check is performed to determine whether the buffer contains all the data necessary to calculate the current position of the cursor, which corresponds to the neural data of the previous second (2048 points). Where this is not the case, the method continues checking the buffer until the buffer is full, step 408. The position of the cursor is updated every 250 ms according to certain embodiments, which means that the buffer always contains 250 ms (512 points) of "new" EEG data for processing, in conjunction with 750 ms (1536 points) of data that was processed in previous time steps. When the buffer is full, the neural processor processes the data using the fixed decoder, step 410, and the fixed decoder calculates or otherwise derives and outputs a control command, step 412, based on the neural signals that it has retrieved and processed using the last collection window.

Upon output of the control command, step 412, software executing on the neural processor instructs the processor to perform a check to determine if the task that the user is executing is complete, step 414. In situations where the user is continuing to interact with an application through use of fixed decoder at the neural processor, step 416, program flow returns to step 406. Accordingly, the neural processor retrieves the data from the buffer again and checks whether the buffer is full, allowing the processor to process the neural signals and output the commands from the decoder. When the active task concludes, the process terminates, step 416.

Figure 5A:
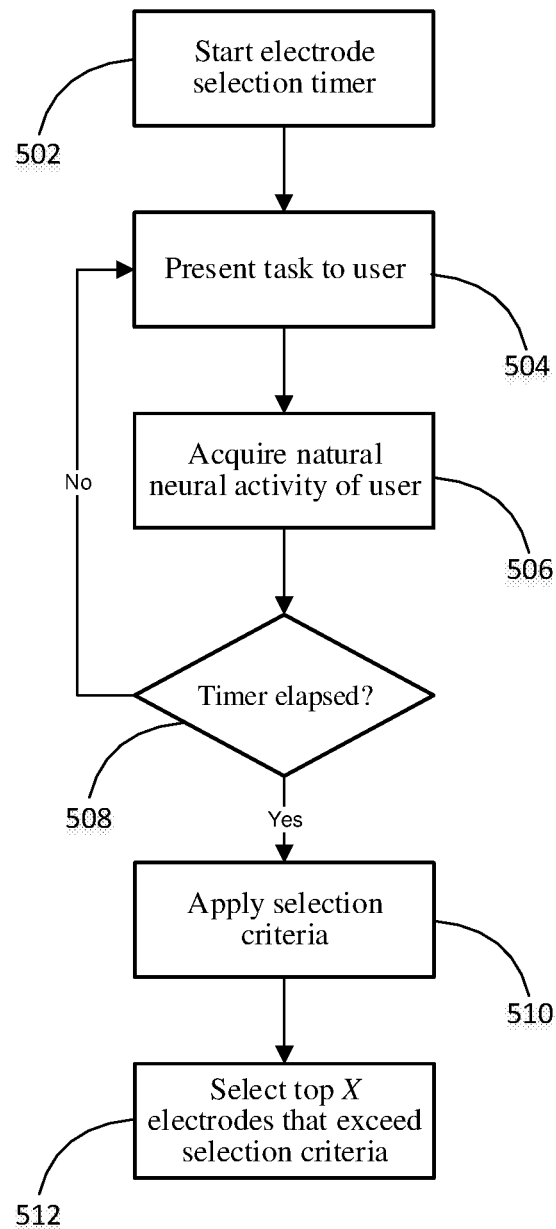
FIG. 5A presents a flow diagram illustrating a method for electrode selection according to one embodiment of the present invention.

When initially using the neural processor in accordance with various embodiments of the present invention, a baseline calculation is performed to select electrodes to be used for the collection of neural signals and to calibrate the neural processor by setting activation thresholds. A subset of available electrodes can be selected for a given user based on baseline neural activity. FIG. 5A sets forth a flow diagram illustrating a method for electrode selection according to one embodiment of the present invention.

According to the process illustrated by FIG. 5A, a method for electrode selection is conducted over a collection and processing window, which is initiated by starting an electrode selection timer. According to one embodiment, the period for collection and processing for electrode selection takes place over a five (5) minute window. While the window is open, i.e., the electrode selection timer has not elapsed, the neural processor presents a task to the user, step 504, and continues to acquire the natural neural activity of the user, step 506. For example, a baseline collection run can be conducted over a five (5) minute window during which the user is asked to look at a display screen where a photo of a task is displayed. During this period the user has no control over the task and the primary purpose of the display is to allow the neural processor to acquire neural signals from the user without providing any feedback to the user. This allows for the acquisition of the natural neural activity of the user.

During task presentment and neural signal acquisition, steps 504 and 506, the system performs a check to determine if the electrode selection timer has elapsed, step 508. Where the electrode selection timer has not elapsed, program flow returns to step 504 whereby the neural processor continues to present the task to the user and collect natural neural activity. Where the timer elapses and collection of neural signals concludes, the collected neural signals are processed in accordance with various selection criteria, step 510. The application of selection criteria is described in greater detail in connection with FIG. 5B.

The selection criteria allows the neural processor to limit its collection of neural signals to a certain number of electrodes that satisfy the selection criteria, step 512. More specifically, where the user is fitted with a plurality of electrodes, the neural processor only selects a certain number of those electrodes that satisfy the selection criteria. For example, assume the user is outfitted with twenty (20) electrodes; the neural processor can select the five (5) electrodes that best satisfy the selection criteria. Alternatively, the method of FIG. 5A can operate in a manner such that the method performs its analysis on various combinations of set of electrodes, as opposed to individual electrodes.

Figure 5B:
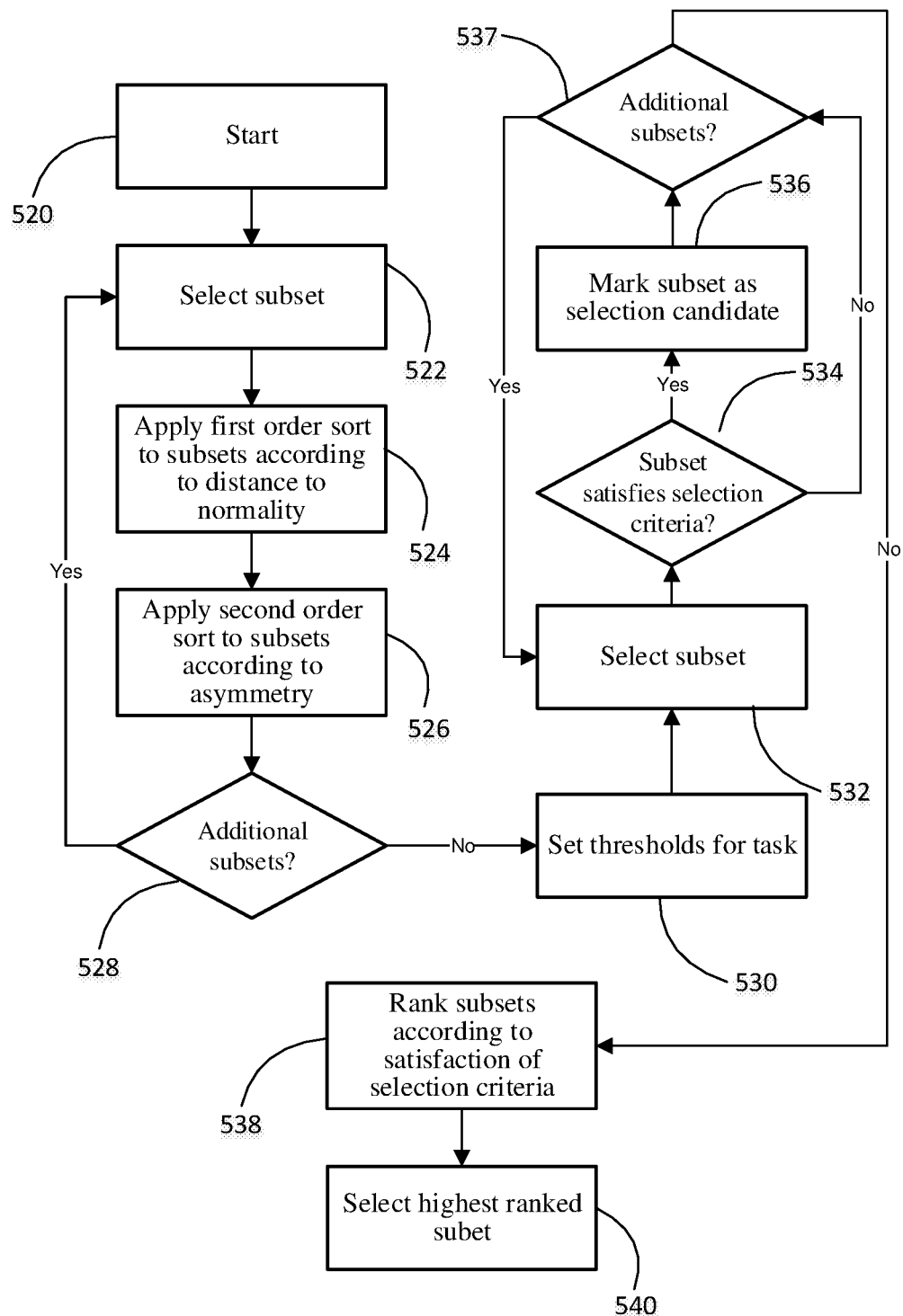
FIG. 5B presents a flow diagram illustrating a method for electrode selection according to another embodiment of the present invention.

FIG. 5B illustrates the application of selection criteria as part of the electrode selection process set forth in FIG. 5A. The process of FIG. 5B begins, step 520, with the selection of a first subset of electrodes under consideration for analysis, step 522. For example, if the subset of electrodes under consideration is five (5) electrodes, and the total set of electrodes under consideration is seventeen (17), the process must perform its analysis on six thousand one hundred and eighty eight (6188) combinations of five electrodes. Accordingly, a first subset of electrodes is selected, step 522, and a first order sort is applied in accordance to the distance to normalcy for a given subset, step 524. According to one embodiment, a one-sample Kolmogorov-Smirnov test is applied to test for normality of the distribution of any sample, which involves standardizing a given sample for comparison with a standard normal distribution.

In addition to the first order sort, step 524, a second order sort is applied to sort the subsets according to skewness, step 526, which is a measure of the asymmetry of the probability distribution of a real-valued variable about its mean. Subsequent to application of the first order sort and the second order sort, steps 524 and 526, respectively, a check is performed to determine if there are any additional subsets of electrodes under consideration that require sorting, step 528. Where there are additional subsets under consideration, processing returns to step 522 with the additional subsets being processed in accordance with the first and second order sorting described herein.

Upon sorting and ordering of the various subsets of electrodes under consideration, steps 522 through 528, the method continues with the setting of specific thresholds for the selection of electrode subsets, step 530. The setting of specific thresholds for the selection of electrode subsets can be arbitrarily based on a subjective "good fit" for a given task and such that they are neither too easy nor too difficult to reach. Accordingly, there is wide variation as to the specific thresholds that a given system can implement. According to one embodiment, and building on the interface that the training applications of FIG. 2 and FIG. 3 present, thresholds can be set for the given task at 2.9 times standard deviation and identifying subsets of electrodes, e.g., subsets of five electrodes, that meet the goal condition for the task a set number of times during initialization. For example, at step 530 and in the context of FIG. 2, the method can identify subsets of electrodes that meet the goal condition for the task (e.g., crossing the upper target line) four times during a five minute period.

Thresholds are set for the task, step 530, and a first subset of electrodes is selected for consideration in accordance with the set thresholds, step 532. The threshold criteria are applied to the subset of electrodes under consideration and a check is performed to determine if the subset under consideration satisfies the set threshold criteria, step 534. Where the subset under consideration meets the threshold criteria for selection, processing proceeds to step 536 with the subset under consideration marked as a selection candidate. Regardless of whether the check that the method performs at step 534 evaluates to true, however, program flow is ultimately directed to step 537, where a check is performed to determine if there are additional subsets under consideration that require analysis vis-à-vis the thresholds set in step 530. Where additional subsets require consideration, a subsequent subset is selected for analysis, step 532.

Because it is possible (although rather remote) that many or all subsets of electrodes under consideration can satisfy the selection criteria thresholds, the method performs a ranking to order the subsets under consideration that satisfy the selection criteria thresholds, step 538. A selection is made, step 540, such that the highest ranked subset is selected as the subset of electrodes that the neural processor can use to collect neural signals for processing and the output of command signals based on the same. When there is an n-way tie for the highest ranked subset of electrodes, step 540, the method can perform an arbitrary selection of any given subset of electrodes in the n-way tie.

Figure 6:
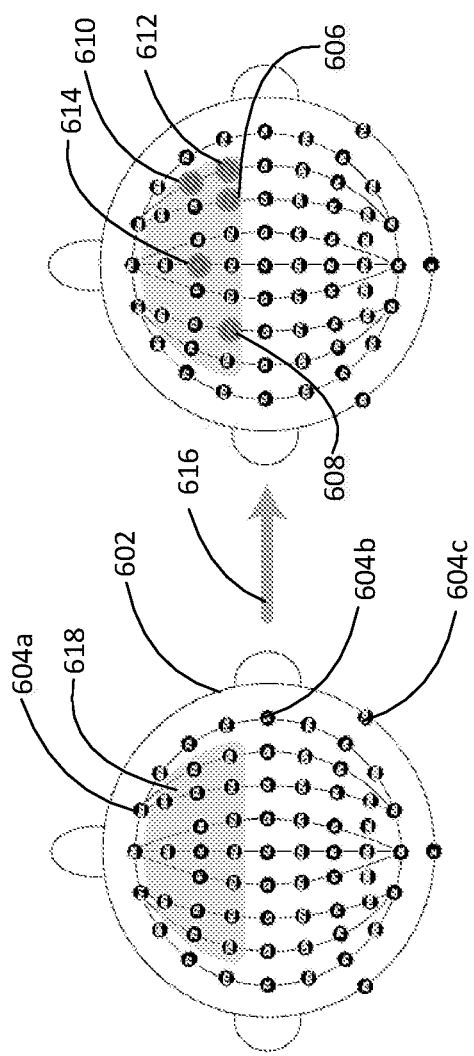
FIG. 6 presents a block diagram illustrating the selection of a subset of electrodes from a set of available electrodes.

Building on the electrode selection methodology (FIG. 5A) and application of selection criteria (FIG. 5B), FIG. 6 presents a block diagram illustrating the selection of a subset of electrodes from a set of available electrodes. According to the embodiment of FIG. 6, a user 602 is outfitted with a number of electrodes, such as electrodes 604a, 604b and 604c, which are displaced in a pattern across the cranium of the user 602. As indicated previously, the set of electrodes, e.g., electrodes 604a, 604b and 604c, can be affixed to the scalp of the user 602 in accordance with various techniques, such as the use of adhesives or affixing the electrodes to a cap or similar garment that is then worn by the user 602.

In accordance with certain embodiments of the invention, only a subset of the total number of available electrodes are analyzed or otherwise interrogated to determine if the quality of the signals received are adequate to drive a BMI using a fixed decoder as described here. By way of the exemplary illustration, there are a set of seventeen (17) electrodes 618 that are under consideration out of the overall set of electrodes (the "analysis set") with which the user 602 has been outfitted. Considering the analysis set, embodiments of the present invention analyze the neural signals from various combinations of subsets of electrodes forming the analysis set, such as subsets of five (5) electrodes. Out of an ensemble of seventeen electrodes in the analysis set, analyzing the neural signals received over a period of time from subsets of five electrode combinations provides a range of six thousand one hundred eighty eight (6188) possible subsets to analyze.

Applying an electrode selection methodology and selection criteria 616, such as those described in connection with FIG. 5A and FIG. 5B, respectively, a subset of five electrodes is selected for use in collection of neural signals in conjunction with operation of the BMI that the neural processor provides. According to the present example, there were initially seventeen electrodes in the analysis set. From the analysis set, a subset of five electrodes were selected that satisfied the selection methodology, which include electrodes 606, 608, 610, 612 and 614. Those of skill in the art recognize that the application of any specific selection methodologies, including those described herein, can result in the selection of a different subset of electrodes for any given user, though it is possible for two disparate users to use the same subset of electrodes.

Figure 7:
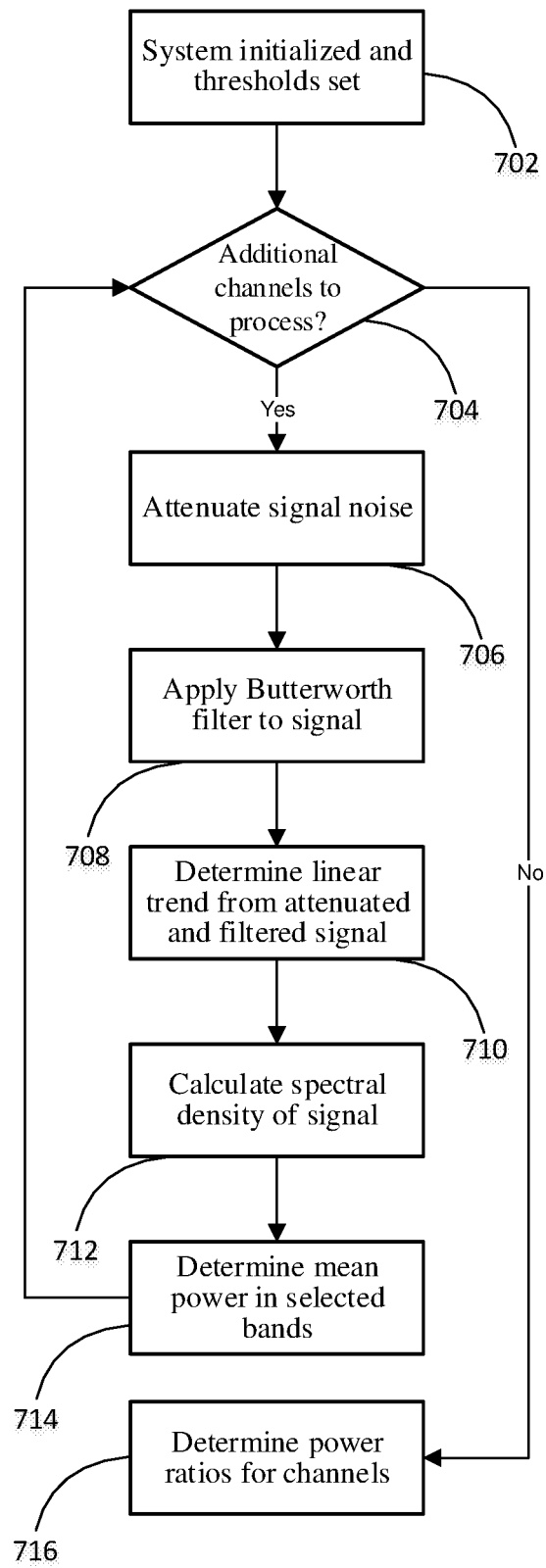
FIG. 7 presents a flow diagram illustrating a method for signal acquisition and processing by a fixed decoder using channel power ratios according to one embodiment of the present invention.

FIG. 7 presents a flow diagram illustrating a method for signal acquisition and processing by a fixed decoder using channel power ratios according to one embodiment of the present invention. According to the present embodiment, a method for determining power ratios for one or more given channels begins with system initialization and the setting of channel selection thresholds, step 702. Contained within this step can also be the selection of a specific set or subset of electrodes from which neural signals are to be acquired for processing by a fixed decoder.

The method continues with a check to determine if there are additional channels to process, step 704, which evaluates to true on the first iteration of the loop and causes selection of a first channel for processing. When step 704 evaluates to true, program flow moves to step 706 in which the method attenuates signal noise on the given selected channel. According to one embodiment, the method implements a notch filter, also referred to as a band-stop or band-rejection filter, to attenuate frequencies around a certain range, e.g., 50 Hz. The method further applies a filter to the signal, which can be a Butterworth filter. According to one embodiment, the Butterworth filter is of order four (4) between one 1 Hz and 50 Hz. The use of a Butterworth filter at step 708 allows incoming neural signals on a given channel to have as flat a frequency response as possible outside of the passband.

According to the embodiment of FIG. 7, the method continues by removing the linear trend or average value from a given neural signal, step 710, which the method can accomplish through the use of a detrend function to remove long-term trends from the incoming neural signal and emphasize short-term changes. Program logic implementing the method performs a calculation to determine the spectral density of the resultant neural signal on the channel, step 712, and the mean power determined for a number of bands contained within the signal, step 714. According to one embodiment, the method calculates mean power for the following bands: beta ($\beta$) (14-24 Hz), gamma ($\gamma$) (30-80 Hz), delta ($\delta$) (1-4 Hz) and theta ($\theta$) (4-8 Hz). Once the method determines the mean power for selected bands in a give channel, step 714, program flow returns to step 704 and the method performs a further check to determine if there are additional channels that require processing.

Upon completion of processing neural signals on the channels made available by the selected subset of electrodes, the method concludes with the determination of power ratios for said channels, step 716. In accordance with one embodiment of the invention, the method of FIG. 7 implements a power ratio in accordance with equation 1 as follows:

$$\text{ratio} = \frac{\gamma \cdot \theta}{\beta \cdot \delta} \quad \text{Equation 1}$$

By utilizing the power ratio of equation 1, the method provides the neural processor with an overall power value for the given channel in accordance with the power levels of the discrete bands under consideration.

Those of skill in the art should appreciate that the method of FIG. 7 does not require any specific ratios or combinations of power of different frequencies of incoming neural signals; the presently described bands' power ratios are by way of example and are not intended to be limiting. Furthermore, the fixed decoder can utilize additional information beyond the power levels of specific bands, e.g., features in the time domain, such as signal amplitudes, etc. The following exemplary pseudocode according to one embodiment of the present invention implements the processing steps set forth in FIG. 7:

```
define Butterworth filter parameters
apply Butterworth filter to signal
define Notch filter parameters apply
Notch filter to signal
% Spectrogram
for iChannel in NChannels
    detrendedSignal=detrend(data(iChannel))
    calculate PSD of detrendedSignal
end
% Compute mean power of bands
beta=mean(psd[14:24]);
gamma = mean(psd[30:80]);
delta = mean(psd[1:4]);
theta = mean(psd[4:8]);
% Compute power ratio
powerRatio=(theta * gamma)/(delta * beta);
position=  log(sum(powerRatio[selectedChannels]));
```

Figure 8:
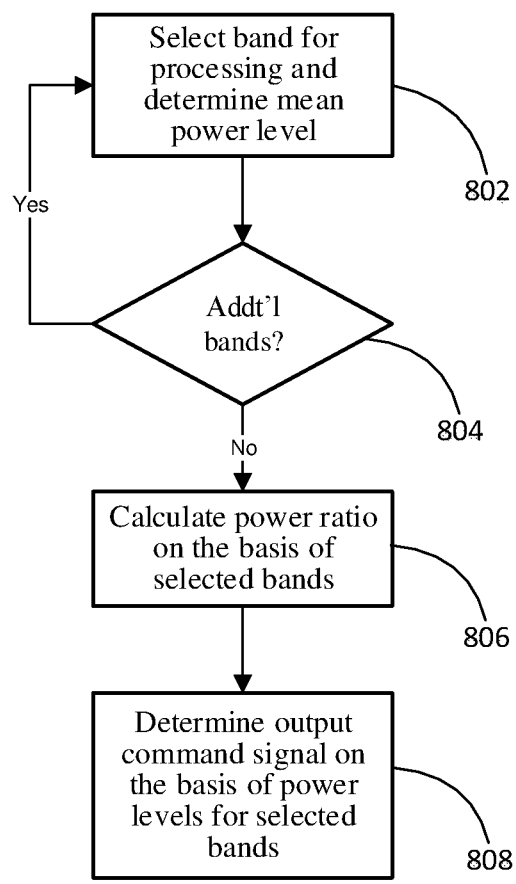
FIG. 8 presents a flow diagram illustrating a process for output of a command according to one embodiment of the present invention.

Embodiments of the present invention utilize power levels of specific bands within a given set of neural signals to generate an output command. FIG. 8 presents one embodiment of a high-level process for determining an output command in view of power levels of specific bands within a given set of neural signals. According to the method of FIG. 8, specific bands within a signal are selected for processing and mean power levels for the bands are determined, steps 802 and 804. Program flow continues with calculating a power ratio for the selected bands across the channels (electrodes) under consideration, step 806. The method uses the power ratios for the channels to determine an output command signal, step 808, which task-specific business logic can utilize to perform a task.

Figure 9:
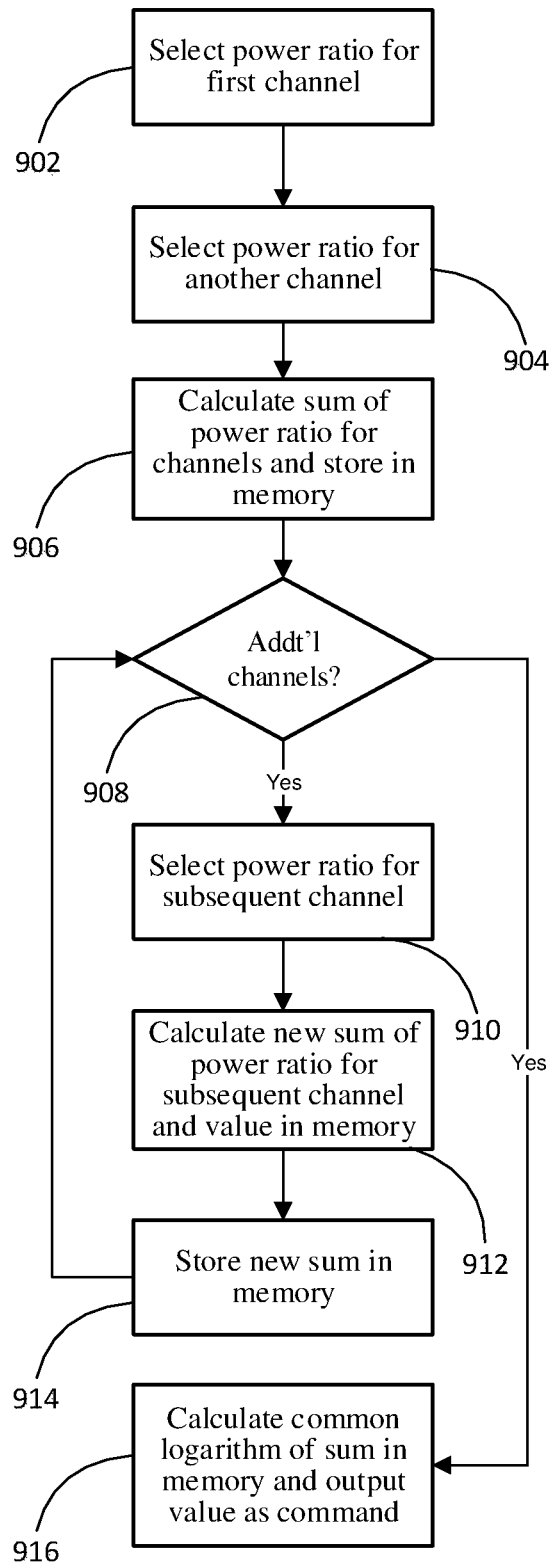
FIG. 9 presents a flow diagram illustrating a method for processing signals by a fixed decoder to determine an output command according to one embodiment of the present invention.

FIG. 9 presents a flow diagram illustrating a method for processing signals by a fixed decoder to determine an output command according to one embodiment of the present invention. According to the embodiment of FIG. 9, the method can begin with the selection of a power ratio for a first channel, step 902, as well as the selection of a power ratio for another channel, step 904. The method calculates the sum of the power ratios for the first channel and the another channel, step 906, storing the sum in a memory structure, such as transient or persistent storage structures.

The method performs a check to determine if there are additional channels for analysis as part of the set of channels under consideration, step 908. Where additional channels are present, the method selects a power ratio for a subsequent channel, step 910. Using the power ratio for the subsequent channel and the value in memory, the method calculates a new sum, step 912, which is then stored back into memory, step 914. Program flow loops according to steps 908 through 914 until the check at step 908 evaluates to false, thereby indicating that no additional channels are present for analysis.

Once the check at step 908 evaluates to false, indicating that no additional channels exist for analysis, program flow continues with the calculation of the common logarithm of the sum in memory, step 916, which is output by the fixed decoder as a command signal. In accordance with one embodiment of the invention, the method of FIG. 9 determines an output command in accordance with equation 2 as follows $$\text{command} = \log\left(\sum_{chn=1}^{n} ratio_{chn(n)}\right) \quad \text{Equation 2}$$

FIGS. 1 through 9 are conceptual illustrations allowing for an explanation of the present invention. Those of skill in the art should understand that various aspects of the embodiments of the present invention can be implemented in hardware, firmware, software, or combinations thereof. In such embodiments, the various components and/or steps would be implemented in hardware, firmware, and/or software to perform the functions of the present invention. That is, the same piece of hardware, firmware, or module of software could perform one or more of the illustrated blocks (e.g., components or steps).

In software implementations, computer software (e.g., programs or other instructions) and/or data is stored on a machine-readable medium as part of a computer program product, and is loaded into a computer system or other device or machine via a removable storage drive, hard drive, or communications interface. Computer programs (also called computer control logic or computer readable program code) are stored in a main and/or secondary memory, and executed by one or more processors (controllers, or the like) to cause the one or more processors to perform the functions of the invention as described herein. In this document, the terms "machine readable medium," "computer program medium" and "computer usable medium" are used to generally refer to media such as a random access memory (RAM); a read only memory (ROM); a removable storage unit (e.g., a magnetic or optical disc, flash memory device, or the like); a hard disk; or the like.

Notably, the figures and examples above are not meant to limit the scope of the present invention to a single embodiment, as other embodiments are possible by way of interchange of some or all of the described or illustrated elements. Moreover, where certain elements of the present invention can be partially or fully implemented using known components, only those portions of such known components that are necessary for an understanding of the present invention are described, and detailed descriptions of other portions of such known components are omitted so as not to obscure the invention. In the present specification, an embodiment showing a singular component should not necessarily be limited to other embodiments including a plurality of the same component, and vice-versa, unless explicitly stated otherwise herein. Moreover, applicants do not intend for any term in the specification or claims to be ascribed an uncommon or special meaning unless explicitly set forth as such. Further, the present invention encompasses present and future known equivalents to the known components referred to herein by way of illustration.

The foregoing description of the specific embodiments will so fully reveal the general nature of the invention that others can, by applying knowledge within the skill of the relevant art(s) (including the contents of the documents cited and incorporated by reference herein), readily modify and/or adapt for various applications such specific embodiments, without undue experimentation, without departing from the general concept of the present invention. Such adaptations and modifications are therefore intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one skilled in the relevant art(s).

While various embodiments of the present invention have been described above, it should be understood that they have been presented by way of example, and not limitation. It would be apparent to one skilled in the relevant art(s) that various changes in form and detail could be made therein without departing from the spirit and scope of the invention. Thus, the present invention should not be limited by any of the above-described exemplary embodiments, but should be defined only in accordance with the following claims and their equivalents.

The invention claimed is:

1. A method for generating an output command by a neural processor through use of an operant learning brain-machine interface, the method comprising:
   selecting one or more electrodes from a plurality of electrodes by program code executing on the neural processor;
   receiving neural signals at the neural processor from the one or more selected electrodes;
   setting thresholds based on the received neural signals;
   setting a timer at the neural processor to define an output command rate;
   while the timer has not elapsed, executing program code by the neural processor for retrieving and processing the received neural signals; and
   calculating a control command through the use of a fixed decoder in the neural processor that receives the retrieved and processed neural signals as input.

2. The method of claim 1 wherein receiving neural signal by the neural processor comprises receiving neural signals from the operant.

3. The method of claim 1 comprising providing the control command by program code executing on the neural processor as an input to a subsequent hardware or software component.

4. The method of claim 1 comprising performing a check by program code executing on the neural processor to determine if a current task is complete.

5. The method of claim 1 comprising setting the timer by program code executing on the neural processor to define a subsequent output command rate and retrieving and processing the received neural signals while the timer has not elapsed.

6. The method of claim 1 wherein selecting one or more electrodes from a plurality of electrodes comprises:
presenting a task to the operant under the control of program code executing at the neural processor;
acquiring neural activity of the operant during presentation of the task by the neural processor;
applying selection criteria by the neural processor to the acquired neural activity; and
selecting by the neural processor one or more electrodes that exceed the selection criteria.

7. The method of claim 6 wherein acquiring neural activity comprises starting an electrode selection timer by program code executing at the neural processor to define a window over which the neural processor is to acquire neural activity.

8. The method of claim 6 wherein selecting by the neural processor comprises selecting a subset of electrodes by the neural processor that exceed the selection criteria.

9. The method of claim 1 wherein processing the received neural signals comprises:
attenuating signal noise on one or more channels contained within the received neural signals;
calculating a spectral density for the one or more attenuated channels; determining
mean power in one or more selected bands for the one or more channels; and
determining power ratios for the one or more channels.

10. The method of claim 9 wherein determining power ratios for a given channel from the one or more channels is determined by program code executing on the neural processor according to calculate the ratio $$\frac{\gamma \cdot \theta}{\beta \cdot \delta}.$$

11. The method of claim 9 wherein calculating the control command comprises program code instructing the neural processor to calculate:

$$\log \sum_{chn=1}^{n} ratio_{chn(n)}.$$

12. Non-transitory computer readable media comprising program code that when executed by a programmable processor causes execution of a method for generating an output command by a neural processor through use of an operant learning brain-machine interface, the program code comprising:
program code for selecting one or more electrodes from a plurality of electrodes by program code executing on the neural processor;
program code for receiving neural signals at the neural processor from the one or more selected electrodes;
program code for setting thresholds based on the received neural signals; program
code for setting a timer at the neural processor to define an output command rate;
program code for and processing the received neural signals by the neural processor while the timer has not elapsed; and
program code for calculating a control command through the use of a fixed decoder in the neural processor that receives the retrieved and processed neural signals as input.

13. The computer readable media of claim 12 comprising program code for providing the control command as an input to a subsequent hardware of software component.

14. The computer readable media of claim 12 comprising program code for performing a check on the neural processor to determine if a current task is complete.

15. The computer readable media of claim 12 comprising program code for setting the timer to define a subsequent output command rate and program code for retrieving and processing the received neural signals while the timer has not elapsed.

16. The computer readable media of claim 12 wherein selecting one or more electrodes from a plurality of electrodes comprises:
program code for presenting a task to the operant;
program code for acquiring neural activity of the operant during presentation of the task by the neural processor;
program code for applying selection criterial by the neural processor to the acquired neural activity; and
program code for selecting, by the neural processor, one or more electrodes that exceed the selection criteria.

17. The computer readable media of claim 16 wherein program code for acquiring neural activity comprises program code for starting an electrode selection timer to define a window over which the neural processor is to acquire neural activity.

18. The computer readable media of claim 16 wherein program code for selecting one or more electrodes comprises program code for selecting a subset of electrodes by the neural processor that exceed the selection criteria.

19. The computer readable media of claim 12 wherein program code for processing the received neural signals comprises:
program code for attenuating signal noise on one or more channels contained within the received neural signals;
program code for calculating a spectral density for the one or more attenuated channels;
program code for determining mean power in one or more selected bands for the one or more channels; and
program code for determining power ratios for the one or more channels.

20. The computer readable media of claim 19 wherein program code for calculating the control command comprises program code for calculating $$\log \sum_{chn=1}^{n} ratio_{chn(n)}.$$

* * * * *